(12) United States Patent
Morhard et al.

(10) Patent No.: US 12,350,341 B2
(45) Date of Patent: Jul. 8, 2025

(54) METHODS FOR THE TREATMENT OF CANCER AND BENIGN LESIONS BY ABLATION

(71) Applicant: Duke University, Durham, NC (US)

(72) Inventors: Robert Morhard, Durham, NC (US); Nirmala Ramanujam, Durham, NC (US); David Katz, Raleigh, NC (US)

(73) Assignee: Duke University, Durham, NC (US)

( * ) Notice: Subject to any disclaimer, the term of this patent is extended or adjusted under 35 U.S.C. 154(b) by 539 days.

(21) Appl. No.: 16/490,227

(22) PCT Filed: Mar. 2, 2018

(86) PCT No.: PCT/US2018/020589
§ 371 (c)(1),
(2) Date: Aug. 30, 2019

(87) PCT Pub. No.: WO2018/160926
PCT Pub. Date: Sep. 7, 2018

(65) Prior Publication Data
US 2019/0381178 A1    Dec. 19, 2019

Related U.S. Application Data

(60) Provisional application No. 62/465,949, filed on Mar. 2, 2017.

(51) Int. Cl.
| | |
|---|---|
| *A61K 47/38* | (2006.01) |
| *A61K 9/00* | (2006.01) |
| *A61K 9/08* | (2006.01) |
| *A61K 31/045* | (2006.01) |
| *A61K 45/06* | (2006.01) |
| *A61K 49/00* | (2006.01) |
| *A61P 17/02* | (2006.01) |
| *A61P 35/00* | (2006.01) |

(52) U.S. Cl.
CPC ............ *A61K 47/38* (2013.01); *A61K 9/0019* (2013.01); *A61K 9/08* (2013.01); *A61K 31/045* (2013.01); *A61K 45/06* (2013.01); *A61K 49/0043* (2013.01); *A61P 17/02* (2018.01); *A61P 35/00* (2018.01)

(58) Field of Classification Search
None
See application file for complete search history.

(56) References Cited

U.S. PATENT DOCUMENTS

| | | | |
|---|---|---|---|
| 4,963,591 A | 10/1990 | Fourman et al. | |
| 6,127,419 A * | 10/2000 | Burzynski ............ | A61K 31/198 |
| | | | 514/563 |
| 2007/0116647 A1 * | 5/2007 | Theron ................... | A61P 43/00 |
| | | | 424/9.42 |
| 2008/0096967 A1 * | 4/2008 | Lopez ..................... | A61P 31/14 |
| | | | 514/567 |
| 2017/0049732 A1 | 2/2017 | Graeber et al. | |

FOREIGN PATENT DOCUMENTS

| | | | |
|---|---|---|---|
| WO | 2016/200672 | 12/2016 | |
| WO | WO-2016200672 A1 * | 12/2016 | .............. A61P 31/12 |
| WO | 2017173178 A1 | 10/2017 | |

OTHER PUBLICATIONS

Sannier et al.(A New Sclerosing Agent in the Treatment of Venous Malformations. Interventional Neuroradiology 10: 113-127, 2004) (Year: 2004).*
Zhang et al.(Endoscopic ultrasound-guided ethanol ablation therapy for tumors. World J Gastroenterol Jun. 14, 2013; 19(22): 3397-3403) (Year: 2013).*
International Search Report and Written Opinion corresponding to PCT/US2018/020589 (mailed May 7, 2018) (7 pages).
"Chapter 2: An introduction to cervical intraepithelial neoplasia (CIN)", Colposcopy and treatment of cervical intraepithelial neoplasia: a beginners' manual, Edited by J.W. Sellors and R. Sankaranarayanan, 2003, 13-19.
Abdul-Karim, F.W. , et al., "Morphometric study of intraepithelial neoplasia of the uterine cervix", Obstetrics and Gynecology 60(2), 1982, 210-214.
Anorlu, Rose , "Cervical cancer: the sub-Saharan African perspective", Reproductive Health Matters 16(32), 2008, 41-49.
Artifon, Everson L.A., et al., "EUS-guided alcohol ablation of left adrenal metastasis from non-small-cell lung carcinoma", Gastrointestinal Endoscopy 66(6), 2007, 1201-1205.
Burns, Robert A., et al., "Tumor-localizing and photosensitizing properties of hematoporphyrin derivative in hamster buccal pouch carcinoma", Oral Surgery, Oral Medicine, Oral Pathology 61(4), 1986, 368-372.
Dewitt, John , et al., "EUS-guided alcohol ablation of metastatic pelvic lymph nodes after endoscopic resection of polypoid rectal cancer: the need for long-term surveillance", Gastrointest Endosc 74(2), 2011, 446-447.
Dompmartin, Anne , et al., "Venous malformation: update on aetiopathogenesis, diagnosis and management", Phlebology 25(5), 2010, 224-235.
Ebara, Masaaki , et al., "Percutaneous ethanol injection for small hepatocellular carcinoma: Therapeutic efficacy based on 20-year observation", Journal of Hepatology 43(3), 2005, 458-464.

(Continued)

*Primary Examiner* — Jake M Vu
(74) *Attorney, Agent, or Firm* — Myers Bigel, P.A.

(57) ABSTRACT

The present disclosure provides methods for the treatment of a lesion, such as a cancerous lesion, a precancerous lesion, or a benign lesion (e.g. a benign lesion on the skin) in a subject comprising administering to the subject a therapeutically effective amount of a therapy solution comprising a viscous carrier and an alcohol or hydrophobic anti-cancer agent, such that the lesion is treated. In some embodiments, the therapy solution includes an ethyl cellulose-ethanol mixture. In some embodiments, the therapy solution is administered to the lesion at a rate of from about 1 mL/hr to about 15 mL/hr.

21 Claims, 8 Drawing Sheets

(56) References Cited

OTHER PUBLICATIONS

Ferlay, Jacques, et al., "Estimates of worldwide burden of cancer in 2008: Globocan 2008", Int J Cancer 127 (12), 2010, 2893-2917.
Heilo, Arne, et al., "Efficacy of Ultrasound-Guided Percutaneous Ethanol Injection Treatment in Patients with a Limited Number of Metastatic Cervical Lymph Nodes from Papillary Thyroid Carcinoma", The Journal of Clinical Endocrinology & Metabolism 96(9), 2011, 2750-2755.
Huang, Guan-Tarn, et al., "Percutaneous Ethanol Injection Versus Surgical Resection for the Treatment of Small Hepatocellular Carcinoma: A Prospective Study", Ann Surg. 242(1), 2005, 36-42.
Jurgensen, Christian, et al., "EUS-guided alcohol ablation of an insulinoma", Gastrointestinal Endoscopy 63(7), 2006, 1059-1062.
Kiricuta Jr., Ion-Christian, et al., "Tissue Water Content and Nuclear Magnetic Resonance in Normal and Tumor Tissues", Cancer Research 35(5), 1975, 1164-1167.
Kuang, Ming, et al., "Ethanol Ablation of Hepatocellular Carcinoma Up to 5.0 cm by Using a Multipronged Injection Needle with High-Dose Strategy", Radiology 253(2), 2009, 552-561.
Linden, Allison F., et al., "Challenges of Surgery in Developing Countries: A Survey of Surgical and Anesthesia Capacity in Uganda's Public Hospitals", World J Surg, 36(5), 2012, 1056-1065.
Mariategui, J., et al., "Comparison of depth of necrosis achieved by CO2- and N2O-cryotherapy", Int J Gynaecol Obstet 100(1), 2008, 24-26.
Netti, Paola A., et al., "Role of Extracellular Matrix Assembly in Interstitial Transport in Solid Tumors", Cancer Research 60(9), 2000, 2497-2503.
Pomfret, Ronald, et al., "The Substitute Brain and the Potential of the Gel Model", Ann Neurosci. 20(3), 2013, 118-122.
Ryu, Munemasa, et al., "Therapeutic Results of Resection, Transcatheter Arterial Embolization and Percutaneous Transhepatic Ethanol Injection in 3225 Patients With Hepatocellular Carcinoma: A Retrospective Multicenter Study", Japanese Journal of Clinical Oncology 27(4), 1997, 251-257.
Shiina, Shuichiro, et al., "Percutaneous ethanol injection therapy for hepatocellular carcinoma. A histopathologic study", Cancer 68(7), 1991, 1524-1530.
Solbiati, L., et al., "Percutaneous ethanol injection of parathyroid tumors under US guidance: treatment for secondary hyperparathyroidism", Radiology 155(3), 1985, 607-610.
Sorajja, Paul, et al., "Outcome of Alcohol Septal Ablation for Obstructive Hypertrophic Cardiomyopathy", Circulation. 118, 2008, 131-139.
Tapani, Erna, et al., "Effect of injection speed on the spread of ethanol during experimental liver ethanol injections", Academic Radiology 3(12), 1996, 1025-1029.
Tapani, Erna, et al., "Toxicity of Ethanol in Low Concentrations: Experimental evaluation in cell culture", Acta Radiol, 37(6), 1996, 923-926.
Tsu, Vivien Davis, et al., "Why the time is right to tackle breast and cervical cancer in low-resource settings", Bull World Health Organ 91(9), 2013, 683-690.
Wang, Yong, et al., "A Novel Method for Viral Gene Delivery in Solid Tumors", Cancer Research 65(17), 2005, 7541-7545.
Wang, Yong, et al., "Effects of rate, volume and dose of intratumoral infusion on virus dissemination in local gene delivery", Mol Cancer Ther 5(2), 2006, 362-366.
Chelales et al. "Radiologic-pathologic analysis of increased ethanol localization and ablative extent achieved by ethyl cellulose" Scientific Reports, 11:20700 (2021).
Morhard et al. "Development of enhanced ethanol ablation as an alternative to surgery in treatment of superficial solid tumors" Scientific Reports, 7:8750 (2017).
Mueller et al. "Optimizing ethyl cellulose-ethanol delivery towards enabling ablation of cervical dysplasia" Scientific Reports, 11(16869) (2021).

* cited by examiner

METHODS FOR THE TREATMENT OF CANCER AND BENIGN LESIONS BY ABLATION

RELATED APPLICATIONS

This application is a 35 U.S.C. § 371 national phase application of International Application Serial No. PCT/US2018/020589, filed Mar. 2, 2018, which claims the benefit of U.S. Provisional Patent Application Ser. No. 62/465,949, filed Mar. 2, 2017, the disclosure of which is incorporated by reference herein in its entirety.

FEDERAL FUNDING LEGEND

This invention was made with Government support under R01-CA193380 awarded by the NIH. The Government has certain rights to this invention.

BACKGROUND

Access to adequate treatment of malignant, premalignant and benign lesions worldwide is often limited by physiological constraints and/or a lack of resources (financial infrastructure, skilled physicians). There is a clear need to increase access to treatment (both in human and veterinary medicine) to improve clinical outcomes and quality-of-life.

As an example, head and neck squamous cell carcinoma (HNSCC) is a substantial cause of global, morbidity and mortality, with an estimated 550,000 new cases and 300,000 deaths each year, and is the sixth leading, cancer worldwide. The vast majority of HNSCC cases occur in Asia and South-East Asia. While tobacco and alcohol consumption are major risk factors for HNSCC worldwide, chewed tobacco, betel nut, and beedi smoking are agents more specific to Asia that result in an increased incidence of HNSCCs in this region of the world. The HNSCC therapeutics market is currently limited by lack of radiation oncologists, surgeons, and overall health care infrastructure.

SUMMARY

Ethanol ablation has previously been used to treat inoperable hepatocellular carcinomas as well as other tumors; however, its efficacy is limited by leakage into nearby tissue and rapid vascular clearance. We have developed an innovative formulation that combines ethanol with ethyl cellulose to control its localization and enhance efficacy. Ethyl cellulose is soluble in ethanol, but forms a stiff gel when it encounters an aqueous environment (tissue), which is referred to here as gel ethanol. A proof-of-concept study has been conducted in a spontaneous model of oral squamous cell cancer (SCC), which demonstrated that the ethanol gel is significantly more effective in treating tumors compared to pure ethanol. To visualize gel ethanol distribution within the tumor, we have added a clinically approved fluorescent dye, fluorescein, into the formulation. Using a hand-held Pocket Scope, a product that we have previously developed, we can visualize gel ethanol distribution in vivo in real time.

While our work demonstrates the safety and efficacy of gel ethanol ablation in HNSCC gel ethanol ablation is not specific to a particular indication or cancer type and could be used to ablate other lesions, including other easily accessible tumors, such as those of the cervix and skin, to name a few examples. Another area where gel ethanol is beneficial is in the treatment of inoperable cancers. Finally, this may be an effective alternative to current ablative techniques for benign skin lesions.

The present disclosure provides a novel method of treating cancer, or a precancerous lesion or benign lesion (such as a skin tag) that is advantageously ultra-low cost, requires no specialized equipment, whose efficacy is not limited to a certain tissue depth.

One aspect of the present disclosure provides a method of treating a lesion or growth in a subject comprising, consisting of, or consisting essentially of administering to the subject a therapeutically effective amount of a therapy solution such that the lesion or growth is treated.

Another aspect of the present disclosure provides a method of reducing a lesion size in a subject comprising, consisting of, or consisting essentially of administering to the subject a therapeutically effective amount of a therapy solution such that the lesion or growth size is reduced.

Yet another aspect of the present disclosure provides a method of ameliorating a lesion or growth in a subject, the method comprising, consisting of, or consisting essentially of administering to the subject a therapeutically effective amount of a therapy solution such that the lesion is ameliorated.

Provided herein according to some embodiments is a method of treating a lesion selected from a cancerous lesion, a precancerous lesion, and a benign lesion or growth (e.g., a benign epithelial lesion such as a benign lesion on the skin such as a wart or skin tag) in a subject comprising administering to the subject a therapeutically effective amount of a therapy solution, said therapy solution comprising a viscous carrier (e.g. from 20 to 200 centipoise (cP) at room temperature (about 25 degrees Celsius)) and an alcohol or hydrophobic agent, such that the cancer or lesion is treated.

As noted above, in some embodiments upon treating, lesion size is reduced.

In some embodiments, the viscous carrier comprises a cellulose ether polymer selected from the group consisting of methyl cellulose, ethyl cellulose, and ethyl methyl cellulose, in some embodiments, the viscous carrier comprises ethyl cellulose. In some embodiments, the concentration of cellulose ether polymer in the solution is about 1% to about 10% by weight (e.g., about 2% to about 7% by weight). In some embodiments, the therapy solution comprises an ethanol-based solution. In some embodiments, the solution comprises an ethyl cellulose-ethanol solution.

In some embodiments, the lesion is a solid tumor. In some embodiments, the lesion is a non-capsulated tumor. In some embodiments, the lesion is a precancerous lesion. In some embodiments, the lesion is a benign growth.

In some embodiments, the lesion is a precancerous lesion such as that of the cervix, head and neck and skin.

In some embodiments, the lesion is selected from a group of benign lesions. Particular examples of such lesions are warts, acrochordon (skin tags).

In some embodiments, the hydrophobic agent is a hydrophobic anti-cancer drug (e.g., chemotherapeutic such as paclitaxel, etoposide and docetaxel photosensitizers such as photofrin, porphyrin derivatives, phthalocyanines, naphthalocyanines and chlorins).

In some embodiments, the therapy solution comprises an alcohol (e.g., ethanol).

In some embodiments, the lesion is selected from the group of cancers consisting of carcinoma, lymphoma, blastoma, and sarcoma. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, liver cancer, bladder cancer, hepatoma, colorectal cancer, uterine cervical cancer, endometrial carcinoma, salivary gland carcinoma, kidney cancer, vulval cancer, pancreatic cancer, thyroid cancer, hepatic carcinoma, skin cancer, melanoma, myeloma, various types of head and neck cancer, Ewing sarcoma and combinations thereof.

In some embodiments, the lesion is an epithelial tumor or precancerous epithelial lesion along a lumen of the body. In some embodiments, the lesion is, a cervical cancer, a head and neck cancer, an oral cancer or a precancerous lesion thereof. In some embodiments, the lesion is a cervical cancer or a cervical precancerous lesion.

In some embodiments, the therapy solution is administered by injection. In certain embodiments, the therapy solution is injected directly into the lesion.

In some embodiments, the therapy solution is injected or infused directly into the lesion at one or more sites.

In some embodiments, the therapy solution is administered at a rate of from about 1 mL/hr to about 15 mL/hr (e.g., about 5, 8, 10 or 12 mL/hr). In certain embodiments, the rate of injection is about 10 mL/hr.

In some embodiments, about 1 mL to about 10 mL, of the therapy solution is administered (e.g., for each of one or more sites in the lesion). In some embodiments, the volume of the injected solution is less than or equal to the tumor volume. In particular embodiments, this reduces the severity of unintended side effects.

In some embodiments, the solution comprises about 1% to about 10% ethyl-cellulose in ethanol (w/w). In some embodiments, the concentration of ethyl-cellulose in ethanol is about 1% to about 6%. In certain embodiments, the concentration of ethyl-cellulose in ethanol is about 3%.

Another aspect of this invention provides a method of visualizing the distribution of the injected solution with the aid of an imaging agent. A particular example is the addition of a fluorescent agent and visualizing with a fluorescent imager. Thus, in some embodiments, the solution further comprises a detectable compound such as a fluorescent compound (e.g. fluorescein or indocyanine green).

In some embodiments, the method further comprises imaging the lesion to monitor distribution of the composition in vivo upon administration, and/or during administration in real time.

In some embodiments, this visualization will be done at the time of treatment and will be used to direct the delivery of the injected solution and the placement of the needle to ensure effective treatment.

Also provided is therapy solution of any preceding claim for use in a method of treating a lesion as in any preceding claim, or for the preparation of a medicament for a method treating a lesion as in any preceding claim.

Yet another aspect of the present disclosure provides all that is disclosed and illustrated herein.

BRIEF DESCRIPTION OF THE DRAWINGS

The foregoing aspects and other features of the disclosure are explained in the following description, taken in connection with the accompanying drawings, herein:

FIG. 3A: The viscosity of ethyl cellulose-ethanol solutions were measured as a function of ethyl cellulose concentration. FIG. 3B: The ratio of the filtered gel, mass to the initial mass of ethyl cellulose added to the solution is plotted as a function of water concentration. As water concentration increases, the polarity of the solution increases and more ethyl cellulose is pushed out of solution and forms a gel. FIG. 3C: A 3% ethyl cellulose-ethanol solution with all ethyl cellulose in solution. Error bars depict standard deviation and each concentration was performed 4 times. FIG. 3D: A mixture of equal parts deionized water (DI) and 3% ethyl cellulose-ethanol solution with some ethyl cellulose, that has undergone a phase transition to form a gel. FIG. 3E: The ethyl cellulose gel isolated from filtering an equal parts DI water. FIG. 3F: The collected gel from the filter paper.

FIG. 5A presents photographs of representative front and side view images of 50 μL, of ethanol and 3% ethyl cellulose-ethanol injected at 10 mL/hr. Images are taken from the perspective with the widest cross-sectional area (Front) and the orthogonal perspective (Side). FIG. 5B presents a graph of the distribution volume for various injection rates. Volume is calculated under the assumption that the volume is ellipsoid. Distribution volume at 30 minutes after injection onset is shown with each rate-viscosity condition performed 7 times. Mean distribution volume of ethyl cellulose solution is higher than ethanol, alone ($p<0.01$). Mean distribution volume of manual injections is lower than every other injection rate ($p<0.01$). Error bars depict standard error.

FIG. 8A: The Pearson's coefficient between normalized tumor volume at day 7 and in vitro distribution volume is 0.62 (not significant) for ethanol. FIG. 8B: For ethyl cellulose, the Pt arson's coefficient is 0.96 ($p<0.05$).

DETAILED DESCRIPTION

Figure 1:
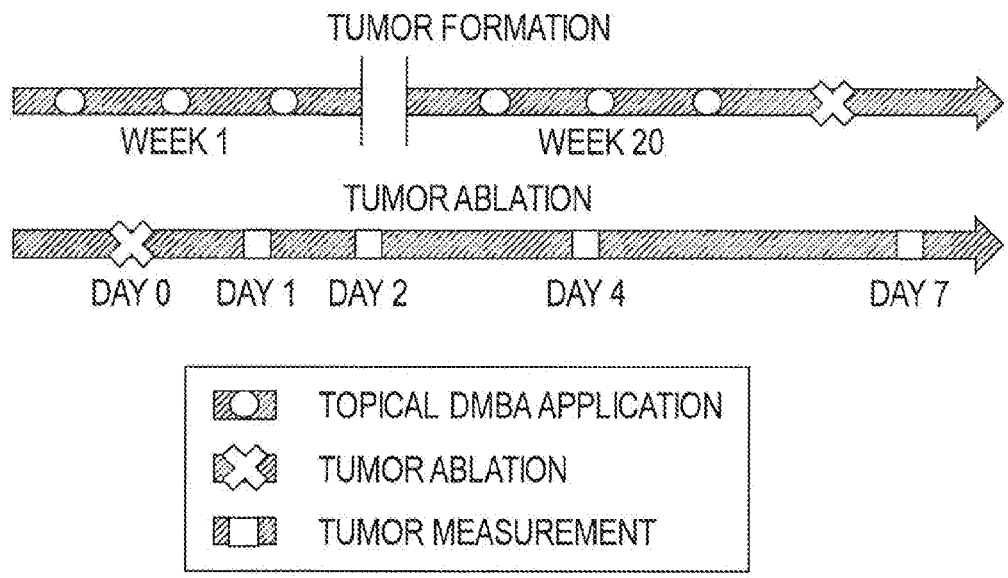
FIG. 1 presents a schematic showing the study design of in vivo assessment of dependence of therapeutic efficacy on injection rate and ethyl cellulose concentration in accordance with an embodiment of the present disclosure. Squamous cell carcinoma tumors, are induced in the hamster cheek pouch through topical application of DMBA 3 times a week until tumors form and reach 100 mm$^3$ (approximately 20 weeks). After tumors form, they are injected with 50 trim$^3$ of either ethanol or 3% ethyl cellulose-ethanol solution at a rate of 0.1, 1.0, 10 or 100 mL/hr. After ablation, tumor volume is measured at 1, 2, 4 and 7 days after treatment. For tumors that did not respond completely and were still present after 7 days, repeat ablations were performed and treated as independent ablations. They were only performed if the tumor volume had increased for two consecutive days.

For the purposes of promoting an understanding of the principles of the present disclosure, reference will now be, made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and van include more than one element.

Unless otherwise defined, all technical terms used herein have the same meaning as commonly understood by one of ordinary skill in the art to which this disclosure belongs.

The present disclosure provides methods of ethanol ablation for the treatment of cancer, precancerous lesions, and tumors in a subject.

One aspect of the present disclosure provides a method of treating cancer, a precancerous growth or benign lesion in a subject comprising, consisting of, or consisting essentially of administering to the subject a therapeutically effective amount of a solution such that the growth or lesion is treated.

Another aspect of the present disclosure provides a method a reducing a lesion size in a subject comprising, consisting of, or consisting essentially of administering to the subject a therapeutically effective amount of a solution such that the tumor size or lesion size is reduced.

Yet another aspect of the present disclosure provides a method of ameliorating a lesion or growth in a subject, the method comprising, consisting of, or consisting essentially of administering to the subject a therapeutically effective amount of a therapy solution such that the lesion is ameliorated.

As used herein, "treatment," "therapy" and/or "therapy regimen" refer to the clinical intervention made in response to a disease, disorder or physiological condition manifested by a patient/subject or to which a patient/subject may be susceptible. The aim of treatment includes the alleviation (e.g., amelioration) or prevention of symptoms, slowing or stopping the progression or worsening of a disease, disorder, or condition and/or the remission of the disease, disorder or condition. In certain embodiments, the treatment comprises the administration of a therapy solution as described herein. It is also within the scope of the present disclosure that treatment may also involve additional therapy and/or treatments (e.g., chemotherapy, radiation, etc., cryo ablation or thermal ablation) in combination with, the administration of the therapy solution provided herein. Such additional treatments may be administered prior to, concurrently with, or post-administration of the therapy solution.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. Preferably, the subject is a human patient is suffering from, or at risk of developing, cancer, precancerous lesions, and/or benign growths.

As is known in the art, a cancer is generally considered as uncontrolled cell growth. As used herein, the term "cancer" refers to any condition characterized by uncontrolled and/or abnormal cell growth (e.g., precancerous lesions/premalignant lesions, such as those found in epithelial tissue of the skin or cervix etc.). In some instances, the cancer/lesion, may be characterized by a tumor formation.

In some embodiments, the lesion is selected from the group of cancers consisting of carcinoma, lymphoma, blastoma, and sarcoma. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, liver cancer, bladder cancer, hepatoma, colorectal cancer, uterine cervical cancer, endometrial carcinoma, salivary gland carcinoma, kidney cancer, vulval cancer, pancreatic cancer, thyroid cancer, hepatic carcinoma, skin cancer, melanoma, myeloma, various types of head and neck cancer, Ewing sarcoma and peripheral and combinations thereof.

In some embodiments, the therapy solution comprises a viscous carrier. In some embodiments, the viscous carrier comprises a cellulose ether polymer selected from the group consisting of methyl cellulose, ethyl cellulose, ethyl methyl cellulose, and combinations thereof, an ethanol-based solution. In some embodiments, the solution comprises an ethyl cellulose-ethanol solution. In some embodiments, the solution comprises another ethanol-soluble, water-insoluble agent as the viscous carrier.

The therapy solutions of the present disclosure can be administered parenterally, for example, intravenously, intra-arterially, intraperitoneally, intrathecally, intraventricularly, intrasternally, intraeranially, intra-muscularly or subcutaneously (including via an array of fine needles or using needle-free Powderject® technology). In yet another embodiment, the therapy solution is administered by injection. In certain embodiments, the therapy solution is injected directly into the cancer/tumor/lesion.

The efficacy of the methods described herein may be enhanced based on the rate and concentration of the therapy solution. Hence, in some embodiments, the rate of injection is about 1 mL/hr to about 15 mL/hr (e.g., about 5, 8, 10 or 12 mL/hr). In certain embodiments, the rate of injection is about 10 mL/hr. In some embodiments, the concentration of viscous carrier (e.g., cellulose ether polymer) is about 1% to about 10% by weight (e.g., about 2% to about 7% by weight). For example, in some embodiments, the concentration of ethyl-cellulose in ethanol is about 1% to about 5% by weight. In certain embodiments, the concentration of ethyl-cellulose in ethanol is about 3% by weight.

In some embodiments, about 1 mL to about 10 mL of the therapy solution is administered (e.g., for each of one or more sites in the cancer/tumor/lesion). In some embodiments, the volume of the injected solution is less than or equal to the tumor volume. In particular embodiments, this may reduce the severity of unintended side effects.

In some embodiments, the therapy solution comprises a detectable compound (e.g., included at about 1, 2 or 3 to 5, 8 or 10% of the solution by weight). In some, embodiments, the detectable compound comprises a fluorescent compound (e.g., fluorescein or indocyanine green). With the detectible compound, the composition may be imaged to monitor the composition's distribution in vivo upon administration, and/or during administration in real time. Apparatus that may be used to visualize the detectable compound include, but are not limited to, those described in WO 2017/173178 to Duke University.

The following examples are provided by of illustration and not by way of limitation.

EXAMPLES

Example 1

Ethanol Ablation for Non-Capsulated Carcinomas

Background: Ethanol ablation has successfully been used in tumor treatment for a variety of applications, beginning with hepatocellular carcinoma and now used in the treatment of cardiomyopathies, parathyroid and pancreatic tumors and metastatic lymph nodes. Despite the wide applicability, little effort has been made to optimize the technique for the treatment of lesions.

Methods: Epithelial squamous cell carcinoma tumors grown in the hamster cheek pouch were treated by intratumoral injection of ablative solutions. Efficacy was determined by monitoring change in tumor volume. Viscosity was increased with addition of ethyl cellulose and injection rate was controlled with an injection pump. A tissue-mimicking mechanical phantom was used to investigate the effect of ethyl cellulose concentration and injection rate on distribution volume. Cellular cytotoxicity was assessed by exposing HeLa cells to ethanol and ethyl cellulose-ethanol solutions.

Findings: Ethyl cellulose-ethanol had a comparable cytotoxicity to ethanol, but a significantly higher volume distribution ($p<0.01$). The standard-of-care of manual pure ethanol injection was ineffective in treatment of epithelial tumors (complete response in 4/13 tumors). Normalized tumor volume decreased dramatically with the addition of ethyl cellulose ($p<0.01$) and reduction, of it rate from manual injections (approximately 100 mL/hr) to 10 mL/hr ($p<0.05$). 6 of 7 tumors treated with ethyl cellulose-ethanol injections at 10 mL/hr responded completely with no lesion present by day 7 and the $7^{th}$ responded by day 8. Lowering rates below 10 mL/hr resulted in lower efficacy. In vivo, ethyl cellulose-ethanol has lower clearance rates as it is ethanol-soluble and water-insoluble and therefore forms a gel upon exposure to water.

Conclusion: Reducing the injection rate and adding ethyl cellulose significantly increased therapeutic efficacy in treatment of epithelial tumors. This is an effective tumor treatment for resource-limited settings as it is low-cost, does not require specialized equipment and can treat larger lesions.

1. Introduction

Ethanol ablation, or the induction of necrosis through protein denaturation and cytoplasmic dehydration via intratumoral ethanol injection, was originally used in the treatment of hepatocellular carcinoma with 5-year survival rates comparable to surgical resection. [Shiina, S., et al., Percutaneous ethanol injection therapy for hepatocellular carcinoma. A histopathologic study. Cancer, 1991. 68(7): p. 1524-30; Ryu, M., et al., Therapeutic results of resection, transcatheter arterial embolization and percutaneous transhepatic ethanol injection in 3225 patients with hepatocellular carcinoma: a retrospective multicenter study. Jpn J Clin Oncol, 1997. 27(4); p. 251-7.] According to the National Cancer Institute, it is a well-established standard treatment option for small (<5 cm), unresectable liver tumors and has low complication rates. [Adult Primary Liver Cancer Treatment (PDQ(R)): Patient Version, in PDQ Cancer Information Summaries. 2002: Bethesda (Md.).] While the liver is the most common context, ethanol ablation has successfully been used in the treatment of cardiomyopathies, [Sorajja, P., et al., Outcome of alcohol septal ablation for obstructive hypertrophic cardiomyopathy. Circulation, 2008. 118(2): p. 131-9] parathyroid, [Solbiati, L., et al., Percutaneous ethanol injection of parathyroid tumors under US guidance: treatment for secondary hyperparathyroidism. Radiology, 1985. 155(3): p. 607-10] pancreatic tumors, [Jurgensen, C., et al, *EUS-guided alcohol ablation of an insulinoma*. Gastrointest Endosc, 2006. 63(7): p. 1059-62] and metastatic lymph nodes, [Arai on E. L., et al., EUS-guided alcohol ablation of let adrenal metastasis from non-small-cell lung carcinoma. Gastrointest Enclose, 2007. 66(6): p. 1201-5; DeWitt, J. and M. Mohamadnejad, EUS-guided alcohol ablation of metastatic pelvic lymph nodes after endoscopic resection of polypoid rectal cancer: the need for long-term surveillance. Gastrointest Endosc, 2011. 74(2): p. 446-7] demonstrating that optimization of this technique will have broad clinical impact.

Ethanol ablation is also poised to have a large impact in resource-limited settings as it is ultra-low cost (<$1), requires no specialized equipment and can effectively treat lesions up to 5 cm. [Kuang, M., et al., Ethanol ablation of hepatocellular carcinoma Up to 5.0 cm by using a multipronged injection needle with high-dose strategy. Radiology, 2009. 253(2): p. 552-61; Ebara, M., et al., Percutaneous ethanol injection for small hepatocellular carcinoma: therapeutic efficacy based on 20-year observation. J Hepatol, 2005. 43(3): p. 458-64; Huang. G. T., et al., Percutaneous ethanol injection versus surgical resection for the treatment of small hepatocellular carcinoma: a prospective study. Ann Surg, 2005. 242(1): p. 36-42; Heilo, A., et al., Efficacy of ultrasound-guided percutaneous ethanol injection treatment in patients with a limited number of metastatic cervical lymph nodes from papillary thyroid carcinoma. J Clin Endocrinol Metab, 201.96(9): p. 2750-5]

One potential shortcoming of ethanol ablation is the reduced efficacy in the treatment of non-capsulated tumors, [Kuang, M., et al., Ethanol ablation of hepatocellular carcinoma Up to 5.0 cm by using a multipronged injection needle with high-dose strategy. Radiology, 2009. 253(2): p. 552-61] or tumors not surrounded by a fibrous capsule.

Our preliminary data demonstrates a dramatic decrease in efficacy in the treatment of epithelial tumors. Additionally, effective tumor ablation often requires large volumes due to leakage into surrounding tissue. [Kuang, M., et al., Ethanol ablation of hepatocellular carcinoma Up to 5.0 cm by using a multipronged injection needle with high-dose strategy. Radiology, 2009. 253(2): p. 552-61] In order to adequately ablate large tumors, multiple injections are necessary and would cause systemic toxicity with high-volume ethanol ablations. While there is some literature reporting the dependence of intratumoral injection efficacy on injection rate, [Wang, Y., et al., Effects of rate, volume, and dose of intratumoral infusion on virus dissemination in local gene delivery. Mol Cancer Ther, 2006. 5(2): p. 362-6] and viscosity, [Wang, Y., et al., A novel method for viral gene delivery in solid tumors. Cancer Res, 2005. 65(17): p. 7541-5] there is unfortunately no existing analysis in the context of ethanol ablation optimization beyond the use of specialized equipment or injecting at rates significantly than manual infections. [Tapani, E., T. Vehmas, and P. Voutilainen, Effect of injection speed on the spread of ethanol during experimental liver ethanol injections. Acad Radiol, 1996.3(12): p. 1025-9]

One example application of an optimized ethanol ablation procedure is the replacement of cryotherapy as the standard-of-care treatment for cervical lesions in resource-limited settings. In 2012 there were 266,000 deaths from cervical cancer worldwide with 86% of these occurring in WHO-classified "Less-developed" regions. [Ferlay, J., et al., Estimates of worldwide burden of cancer in 2008: GLOBOCAN 2008. Int J Cancer, 2010. 127(12): p. 2893-917] Women in regions of "Low Human Development" are over 75% more likely to die from cervical cancer than women in regions of "Ugh Human Development" One cause for this disparity is the discrepancy in treatment options. In regions of "High Human Development" more severe cervical lesions are treated with loop electrosurgical excision procedure (LEEP), in which abnormal tissue is excised with an electrified wire, and less severe lesions are treated with cryotherapy, in which compressed gas and a metal probe are used to freeze abnormal tissue. [in WHO Guidelines for Screening and Treatment of Precancerous Lesions for Cervical Cancer Prevention. 2013: Geneva] in regions of "Low Human Development" the availability of both cryotherapy and LEEP is relatively low. [Anorlu, R. I., Cervical Cancer: the sub-Saharan African perspective. Reproductive Health Matters, 2009. 16(32): p. 41-49] LEEP is restricted to higher-level facilities due to the high initial cost (>$5,000), need for uninterrupted power, and trained personnel. [PATH. Treatment Technologies for Precancerous Cervical Lesions in Low-Resource Settings: Review and Evaluation. Cervical cancer screening and treatment in low-resource settings: practical experience from path 2013]

Cryotherapy, while cheaper (>$1,000) and not dependent on a power grid, requires specialized equipment and hard-to-supply compressed gas tanks. [Tsu, V. D., J. Jeronimo, and B. O. Anderson, Why the time is right to tackle breast and cervical cancer in low-resource settings. Bull World Health Organ, 2013. 91(9): p. 683-90] Additionally, it is ineffective in the treatment of high-grade precancerous lesions (CIN III) as 95% of lesions extend up to 3.6 mm into the cervix [Abdul-Karim, F. W., et. al., Morphometric study of intraepithelial neoplasia of the uterine cervix. Obstet Gynecol, 1982. 60(2): p. 210-4] and $CO_2$ cryotherapy reaches a mean depth of 3.4 mm. [Mariategui, J., et al., Comparison of depth of necrosis achieved by $CO_2$- and $N_2O$-cryotherapy. Int Gynaecol Obstet, 2008, 100(1): p. 24-6] The lack of trained medical personnel and sterile infrastructure exclude surgical intervention. [Linden, A. F., et al., Challenges of surgery in developing countries: a survey of surgical and anesthesia capacity in Uganda's public hospitals. World J Surg, 2012. 36(5): p. 1056-65] Given the constraints, it is clear that we need a new strategy to treat cervical cancer at the point-of-care in developing countries.

Ethanol ablation is also poised to have a large impact in resource-limited settings as it is ultra-low cost (<$1), requires no specialized equipment and can effectively treat lesions up to 5 cm. [Kuang, M., et al., Ethanol ablation of hepatocellular carcinoma Up to 5.0 cm by using a multipronged injection needle with high-dose strategy. Radiology, 2009. 253(2): p. 552-61; Ebara, M., et al., Percutaneous ethanol injection for small hepatocellular carcinoma: therapeutic efficacy based on 20-year observation. J Hepatol, 2005, 43(3): p. 458-64; Huang, G. T., et al., Percutaneous ethanol injection versus surgical resection for the treatment of small hepatocellular carcinoma: a prospective study. Ann Surg, 2005. 242(1): p. 36-42; Heilo, A., et al., Efficacy of ultrasound-guided percutaneous ethanol injection treatment in patients with a limited number of metastatic cervical lymph nodes from papillary thyroid carcinoma. J Clin Endocrinol Metab, 2011. 96(9): p. 2750-5]

This study investigates the dependence of ethanol ablation therapeutic efficacy on injection rate and viscosity. We hypothesized that efficacy is a function of distribution volume of the injected solution and we used a tissue-mimicking mechanical phantom (Pomfret, R., G. Miranpuri, and K. Sillay, The substitute brain and the potential of the gel model. Ann Neurosci, 2011.20(3): p. 118-22) to investigate how this depended on viscosity and rate. To vary injection rates, we used a commercially available syringe pump. To increase viscosity in situ and still allow for the use of a small gauge needle we investigated the use of ethyl cellulose, an ethanol-soluble and water-insoluble cellulose-derivative that forms a gel upon introduction to the aqueous tumor environment (Dompmartin, A., M. Vikkula, and L. M. Boon, Venous malformation: update on aetiopathogenesis, diagnosis and management. Phlebology, 2010. 25(5): p. 224-35) but does not alter cellular cytotoxicity. Mechanical phantom results were verified through ablation of tumors induced via the 7, 12-dimethylbenzanthracene (DMBA)-painted hamster cheek pouch model of the dysplasia carcinoma sequence. Burns, R. A., et al., Tumor-localizing and photosensitizing properties of hematoporphyrin derivative in hamster buccal pouch carcinoma. Oral Surg Oral Med Oral Pathol, 1986. 6.1(4): p. 368-72. We found significant improvements upon the standard-of-care through the addition of ethyl cellulose (and therefore increasing viscosity) and the optimization of injection rate. We were found excellent agreement between in vivo and mechanical phantom results. These observations are the foundation of a novel and effective ablation treatment.

2. Materials and Methods

2.1. In Vitro Viability Study

Low passage HeLa human cervical carcinoma cells (ATCC) were maintained with Eagles minimum essential medium (MEM, Gibeo, Carlsbad, California) supplemented with 10% (vol.) fetal bovine serum, 1% (vol.) penicillin and 1% (vol.) streptomycin. Cells were passaged twice per week and maintained at 37° C. and 5% $CO_2$. Cells were cultured in two 12-well plates and grown to 80% confluence. Immediately before the experiment, cell media was removed and 0.5 mL of fresh media was added to each well. Next, each well was treated with 0.5 mL of either ethanol (200 proof, Koptec, King of Prussia, PA), 3% (w/w) ethyl cellulose (USP, Sigma Aldrich, Rockville, MD) in ethanol or PBS (control), added directly to the media. The plates were then incubated at room temperature for 15 seconds, as this time point has been shown to cause a partial response to ethanol. Tapani, E., et al., Toxicity of ethanol in low concentrations. Experimental evaluation in cell culture. Acta Radiol, 1996. 37(6): p. 923-6. The media containing the treatment solution was then removed, each well was rinsed twice with 1 mL of PBS, and given 1 mL of fresh MEM media. After all wells had been treated, each well was rinsed one time with 1 mL of PBS, given 250 µL of 0-5% trypsin (Gibed, Carlsbad, CA), and returned to the incubator for 5 minutes. Once cells had lifted, 750 µL of media was added to each well and the contents of each well were placed in vials and vortexed. Viability was then assessed with a trypan blue exclusion assay (Gibco, Carlsbad, CA and a Countess Automated Cell Counter, Invitrogen, Carlsbad, CA). Two viability measurements (viability=live cell count/total cell count) were obtained for each well and averaged. There were n=8 wells for each treatment group.

2.2. Solution Preparation and Injection

Three percent ethyl cellulose (Sigma Aldrich)-ethanol solutions (weight by weight) were prepared by stirring at room temperature. Three percent was chosen as higher viscosities required a lockable needle to stay attached to the syringe at high injection rates. Two drops of blue food dye were added for every 1 mL of ethanol and ethyl cellulose-ethanol solutions to enhance contrast. 50 µL of either solution was injected at a rate of 0.1, 0.5, 1.0, 5.0, 10 or 35 mL/hr as controlled by a syringe pump (NE-300 Just Infusion Syringe Pump). Manual injections were approximately 100 mL/hr. A 1 mL syringe and 27 G needles connected with microtubing (Tygon Microtube Tubing, 0.25 mmID) were used for injections. On the outflow-end of the catheter tube a 27 G needle was snapped off the base to fit into the tubing.

2.3. Ethyl Cellulose-Ethanol Solution Characterization

Solution viscosity was measured at room temperature with a Brookfield Model RV-DVIII Ultra Programmable Rheometer (Brookfield Engineering, Middleboro, MA). The cone number was a CP-40. Data values were only considered for torques between 10 and 100%. The last 3 viscosity measurements of each speed were averaged together. All viscosity measurements for each ethyl cellulose concentration were averaged together to produce the final value.

Gel formation rate was determined by adding solutions to 15 mL centrifuge tubes (Falcon, Corning NY), allowing them to reach equilibrium over an hour, filtering the solution with filter paper (Coffee Filter, Harris Teeter, Matthews, NC), collecting gel with a scoopula and weighing. Each ethyl cellulose-ethanol and water mixture was performed 4 times.

2.4. Mechanical Phantoms

Mechanical phantoms were made of 0.2% agarose (Ultra-Pure Agarose from ThermoFisher, solutions were weight by volume) by stirring agarose powder into deionized water over a hot plate until clear and cooling at 4° C. for 24 hours to solidify. Thirty minutes after the onset of the injection, an image was taken with the widest cross-sectional area of dye orthogonal to the camera. The container was then rotated 90 degrees to calculate the depth and imaged again. Images were taken with a ruler in-plane. Each phantom was performed 7 times. To calculate the distribution volume, MATLAB was used to segment the blue dye. The volume was calculated by assuming the morphology was ellipsoid and using the formula $V=4/3*Area_{cross-section}*R_{orhogonal}$. Only dye 3.6 mm above or below the tip of the needle was measured to mimic distribution within a 200 $mm^3$ tumor. Liquid that extends above or below this tumor volume will leak out of the tumor in vivo.

2.5. Hamster Cheek Pouch Model of Squamous Cell Carcinoma

The animal study protocol was approved by the Duke University Institutional Animal Care and Use Committee. For the manual pure ethanol ablation study, a total of 6 hamsters were used. For the rate- and viscosity-controlled study, a total of 8 hamsters were used. Tumors were induced through the topical application of dimethylbenz[a]anthracene (Sigma-Aldrich). Burns, R. A., et al., Tumor-localizing and photosensitizing properties of hematoporphyrin derivative in hamster buccal pouch carcinoma. Oral Surg Oral Med Oral Pathol, 1986. 61(4): p. 368-72. Three times a week the buccal mucosa of each cheek pouch was inverted then stretched from the mouth. An area of approximately 5 $cm^3$ was painted with a cotton swab dipped in the DMBA-mineral oil solution. The cheek pouches were painted until tumors of at least 100 uL in volume developed, at approximately 22 weeks.

2.6. High-Volume Manual Pure Ethanol Ablation

Figure 9:
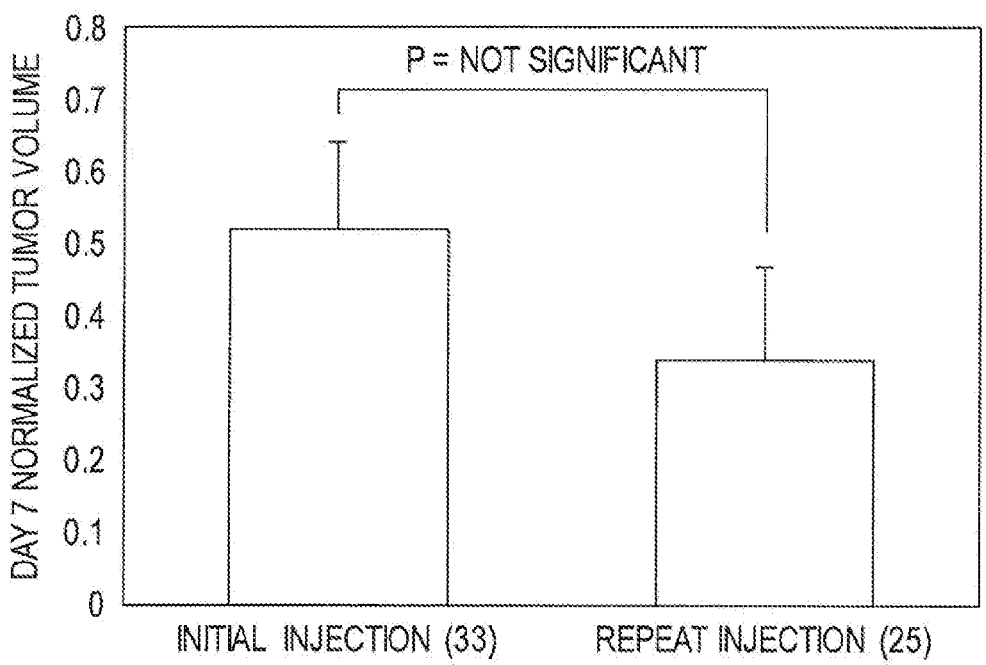
FIG. 9 presents a graph showing the analysis of the effect of repeat injection on efficacy in accordance with an embodiment of the present disclosure. Sample sizes are shown in parenthesis and error bars depict standard error. P-value was greater than 0.30. In the rate- and viscosity-controlled injections, 40% of ethyl cellulose-ethanol injections and 35% of ethanol injections were repeat injections.

The average initial tumor volume was 137±341 µL and a volume of 285±350 µL of a mixture of food dye-ethanol was injected with the needle placed approximately in the center of the tumor. Tumor volumes were measured before the injection and daily for 7 days after. For tumors that didn't respond completely and were still present after 7 days, repeat ablations were performed and treated as independent ablations as though they were new tumors (FIG. 9). They were only performed if the tumor volume had increased for two consecutive days after the 7 day observation period. Volumes were calculated by measuring the longest axis and the orthogonal axis and using the following formula: $V=4/3\pi*(R_{long}^2)*(R_{orth})$. Complete response is defined as the total absence of any evidence of a tumor or raised lesion by visual examination. Thirteen injections were performed in 6 hamsters.

2.7. Injection Rate- and Viscosity-Controlled Study

The average tumor volume was 195±140 µL and 50 µL of solution (either ethanol or 3% ethyl cellulose-ethanol) was injected. Solutions were injected with the syringe pump at 0.1, 1.0 or 10 mL/hr or injected manually. Tumor volume was measured before injections and at 1, 2 4 and 7 days following the injection. For tumors that didn't respond completely and were still present after 7 days, repeat ablations were performed and treated as independent ablations as though they were new tumors (FIG. 9). 36 total ablations were performed on 8 animals. Study design is summarized in FIG. 1.

2.8. Statistical Analysis

For cell viability analysis, a one-Way ANOVA was used followed by a Tukey-HSD. For both phantom distribution volume and in vivo normalized tumor volume analysis, a non-parametric ANOVA was used (Kruskal-Wallis) followed by a non-parametric multiple comparisons test (Dunn's test). In comparing phantom distribution volume and in vivo normalized tumor volume, the Pearson's product moment correlation coefficient was calculated. All statistical analysis was performed in R. Normalized tumor volume was calculated by dividing by the volume at a given time point by the initial volume before treatment.

3. Results

3.1. Low Therapeutic Efficacy was Achieved with Manual Ethanol Ablation

Figure 2:
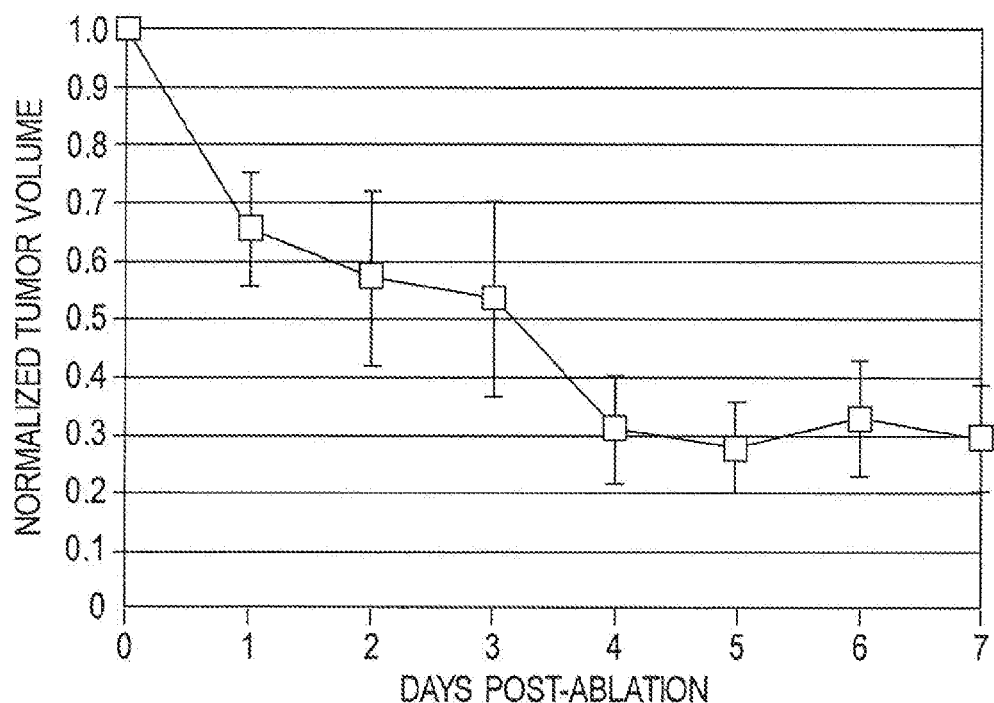
FIG. 2 presents a graph showing the therapeutic efficacy of high-dosage manual ethanol ablation of epithelial tumors in accordance with an embodiment of the present disclosure. Thirteen squamous cell carcinoma tumors were ablated and the tumor volume was measured for 7 days. At day 7, the average tumor volume was 30% of the initial volume and 4 of 13 tumors had responded completely with no sign of a tumor at this time point. Error bars depict standard error. Normalized tumor volume is defined as tumor volume at specified time point divided by initial volume.

For most injections (intratumoral injection of pure ethanol by hand), some necrosis is visible and the overall tumor volume did decrease, but a consistent complete response was not achieved. In total, 13 tumors with an average initial volume of 137±341 µL (mean and standard deviation) were injected with an average of 284±350 µL of pure ethanol. The normalized tumor volume over the course of 7 days after the injection is shown in FIG. 2. On average, tumor volume decreased to 30±33% of the initial volume by day 7. Of the 13 unique tumors ablated, 4 regressed completely and had no visible lesion at day 7.

3.2. Characterization of Ethyl Cellulose-Ethanol Solution

Figure 3A:
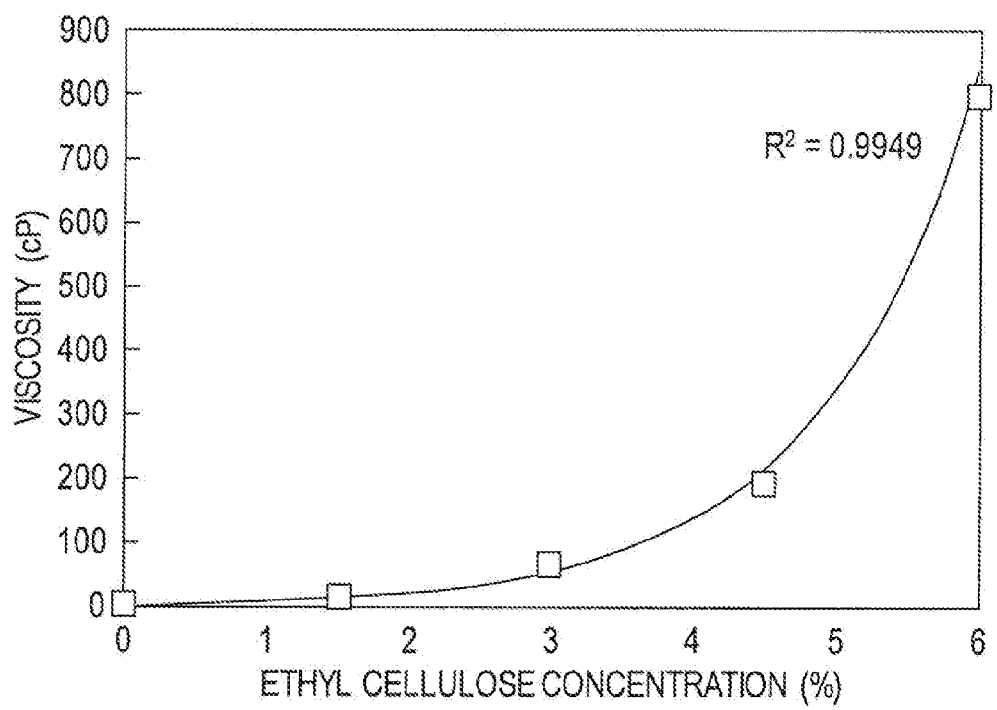
FIG. 3A-FIG. 3F present photographs and graphs showing the characterization of ethyl cellulose-ethanol solution and ethyl cellulose gel formation in accordance with an embodiment of the present disclosure.
Figure 3B:
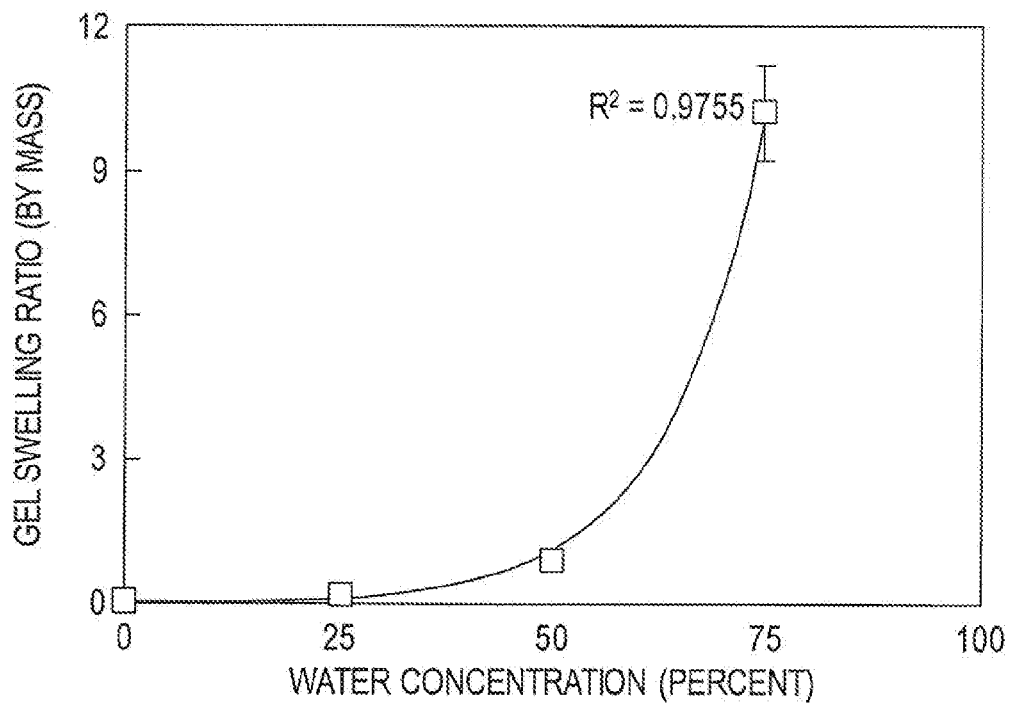
Figure 3C:
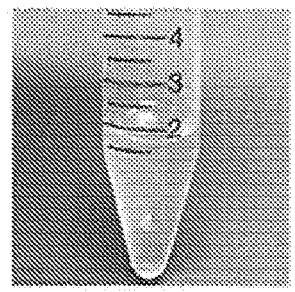
Figure 3E:
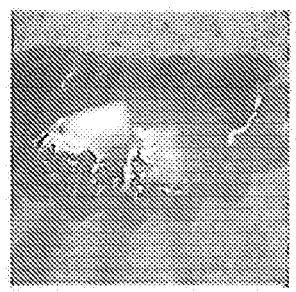
Figure 3D:
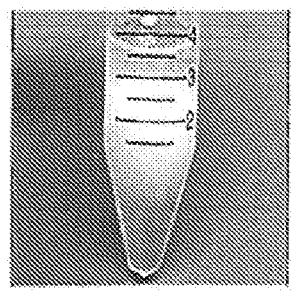
Figure 3F:
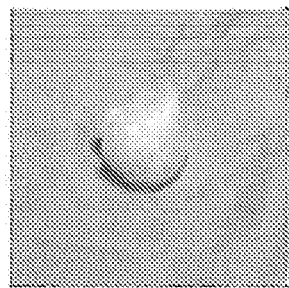
Figure 4:
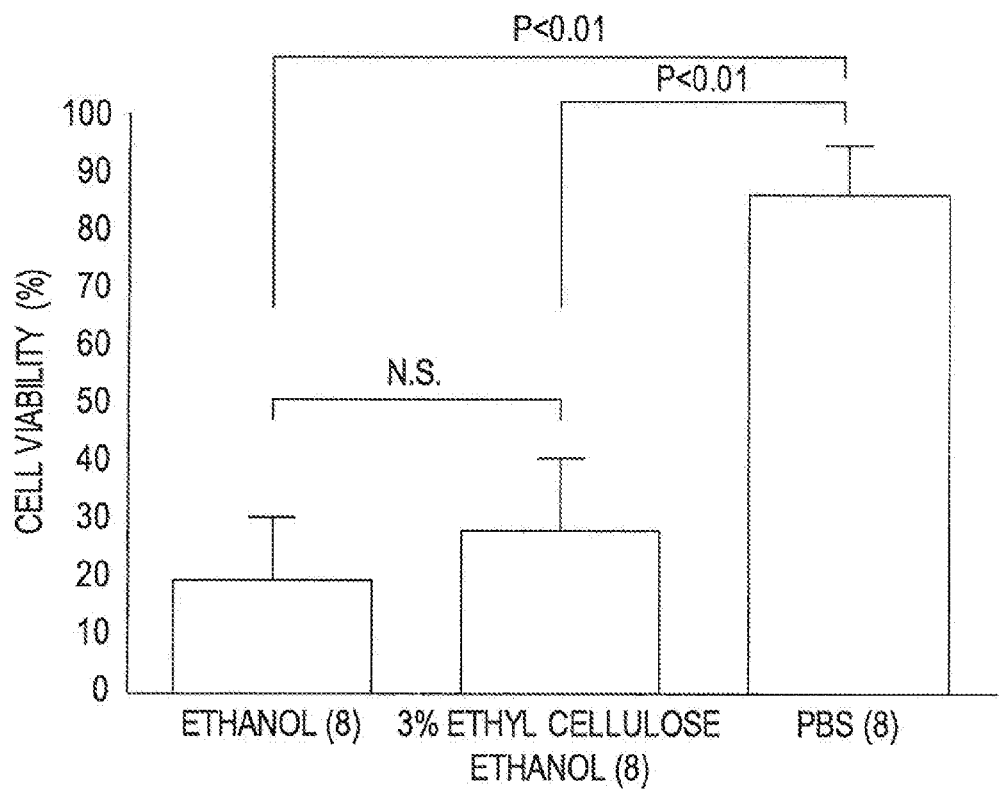
FIG. 4 presents a graph showing the impact of ethyl cellulose on cell viability in accordance with an embodiment of the present disclosure. Ethanol, 3% ethyl cellulose-ethanol and PBS were added to HeLa cells for 15 seconds and viability was assessed. Error bars represent standard deviation, and sample size is denoted in parentheses.

FIG. 3A shows the exponential increase in viscosity with the increase of ethyl cellulose concentration. FIG. 3B depicts the relationship between gel swelling ratio, defined as the mass of the resulting gel divided by the initial mass of ethyl cellulose added to ethanol, and water concentration. As more water is added to ethanol, the liquid phase becomes more polar and the ethyl cellulose solubility decreases, resulting in more gel formation. High water concentrations (>50%) cause the gel to swell to a mass greater than the initial mass added to solution. It is likely absorbing ethanol and excluding water. FIG. 3C shows a clear 3% ethyl cellulose-ethanol solution with no gel formation. In FIG. 3D, 2 mL of DI water has been added to 2 mL of 3% ethyl cellulose-ethanol solution and some opaque gel can be seen floating in the solution. In FIG. 3E, the contents are being filtered and the gel can be seen on top of the filter paper. The gel is then collected (FIG. 3F) and massed.

3.3. In Vitro Cytotoxicity of Ethanol and 3% Ethyl Cellulose-Ethanol

Viability is significantly lower for ethanol and 3% ethyl cellulose-ethanol at 19 and 28%, respectively, as compared to 86% for PBS (p<0.01). No significant difference was found between ethanol and 3% ethyl cellulose-ethanol.

Figures 5A, 5B:
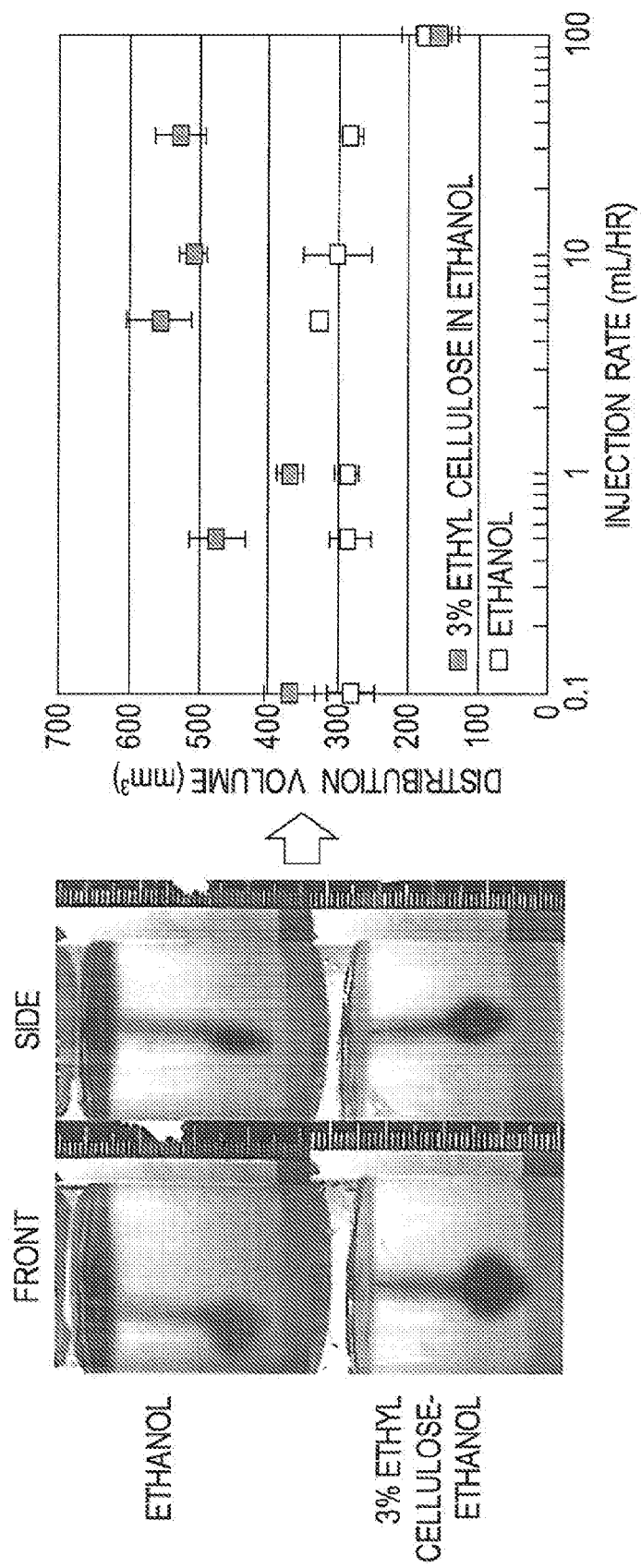
FIG. 5A-FIG. 5B show the dependence of therapeutic efficacy on injection rate and ethyl cellulose concentration in accordance with an embodiment of the present disclosure.

3.4. Analysis of Distribution Volume of Variable-Rate Infections of Ethanol and 3% Ethyl Cellulose-ethanol with a Mechanical Phantom Distribution volume was measured with agarose gel as a tissue-mimicking mechanical phantom. Agarose gels were chosen because, like tissue, they are water-based and poroelastic. Representative images from both perspectives next to an in-plane scale bar with blue food dye used for segmentation of the volume are shown in FIG. 5A. The dependence of distribution volume on injection rate and ethyl cellulose concentration is shown in FIG. 5B. The distribution volume for 3% ethyl cellulose-ethanol has a mean of 421±350 mm$^3$ as compared to 278±247 mm$^3$ for pure ethanol at 30 minutes after injection onset (p<0.01). Manual injections have the lowest distribution volume of 168±82 mm$^3$ and were significantly worse than all other rates (p<0.05). Injections at 5, 10 and 35 mL/hr had distribution volumes of 443±146 mm$^3$, 406±143 mm$^3$ and 407±145 mm$^3$, respectively, and were all significantly higher than the mean distribution volume for all rates (p<0.05).

3.5. Dependence of Therapeutic Efficacy on Infection Rate and Ethyl Cellulose Concentration In order to determine the effect of ethyl cellulose concentration and injection rate on therapeutic efficacy, ablations were performed on tumors in the hamster cheek pouch at a rate of 0.1, 1.0, 10 and 100 mL/hr with either 3% ethyl cellulose-ethanol or pure ethanol. An ablation is defined as an intratumoral injection followed by a 7-day observation period with no additional injections in between. For each testing condition (injection rate/ethyl cellulose concentration), 5 separate tumor ablations were performed. In the case of 3% ethyl cellulose-ethanol injections at 0.1, 1.0 and 10 mL/hr, 7 independent tumor ablations were performed. The time course of tumor response is reported in FIG. 6A-FIG. 6B.

Figure 6A:
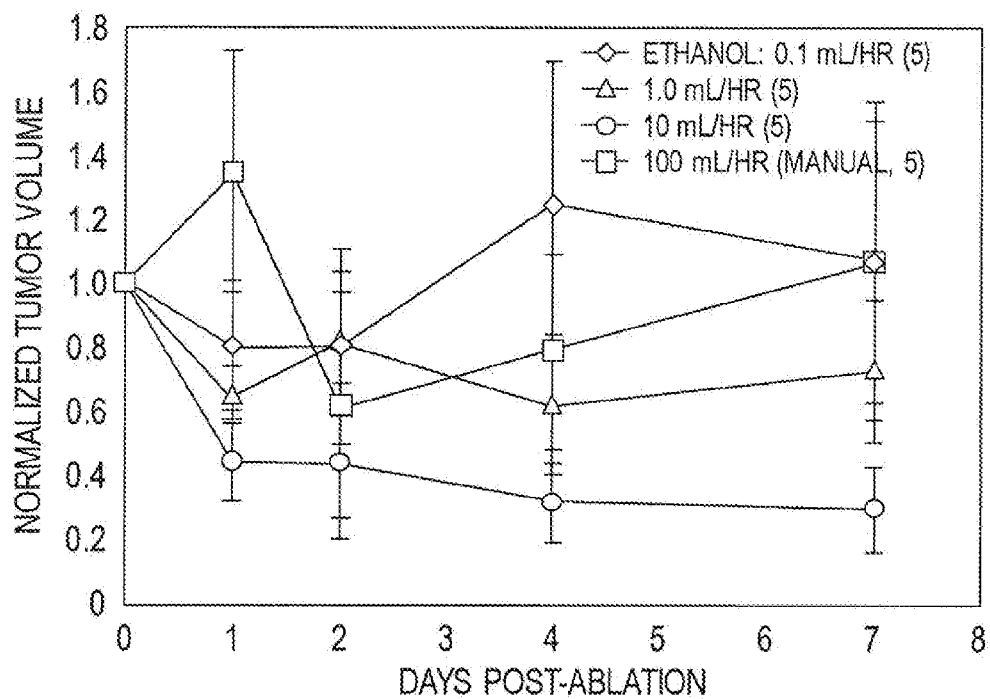
FIG. 6A-FIG. 6B present graphs showing time-course of tumor volume response as a function of injection rate and viscosity in accordance with an embodiment of the present disclosure. Normalized tumor volume measured up to day 7 is shown for ethanol (FIG. 6A) and 3% ethyl cellulose-ethanol (FIG. 6B). Normalized tumor volume is defined as tumor volume at specified time point divided by initial volume. Average initial rumor volume was 195±140 mm³ and injected volume was kept constant at 50 mm³. Error bars depict standard error and sample size is denoted in the legend.
Figure 6B:
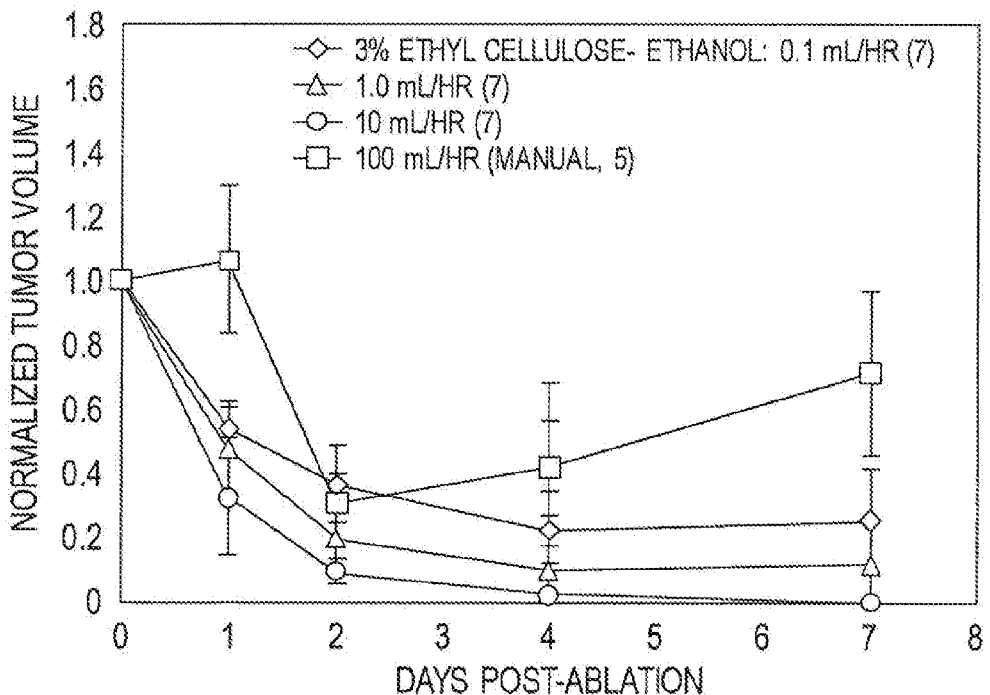
Figure 7:
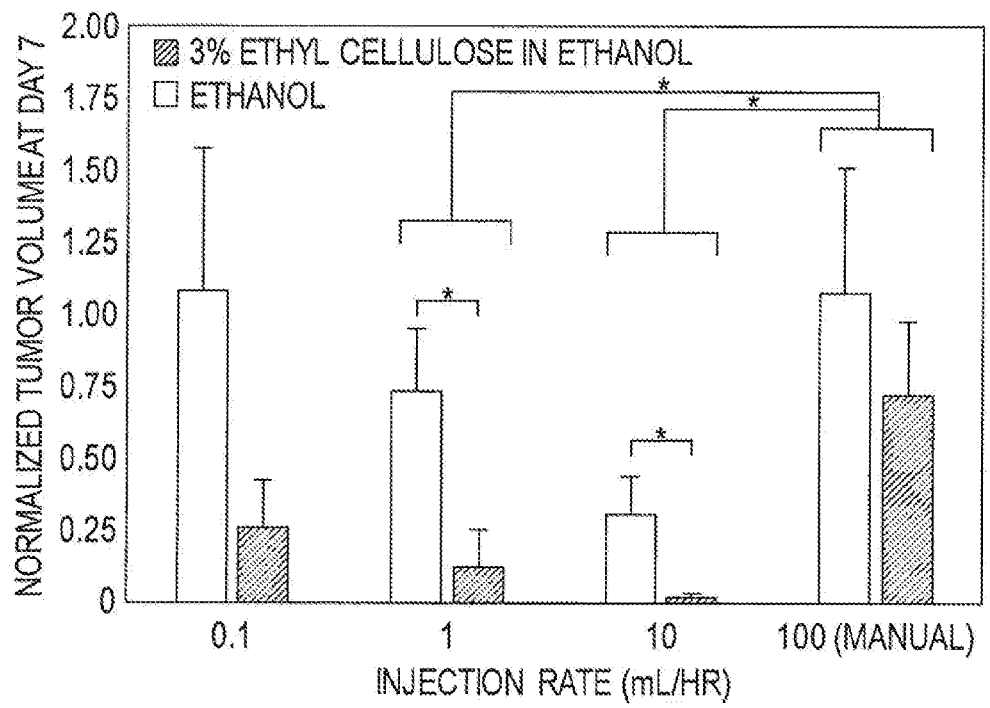
FIG. 7 presents a graph showing the dependence of therapeutic efficacy on ethyl cellulose concentration and rate in accordance with an embodiment of the present disclosure. Normalized tumor volumes at day 7 are provided for each ethyl cellulose concentration—rate combination. 3% ethyl cellulose-ethanol injections are more effective than ethanol injections ($p<0.01$), and both 1.0 and 10 mL/hr injections are more effective than 100 (approximate rate of manual injections, current standard-of-care) injections ($p<0.05$). Error bars depict standard error. Each condition (injection rate/ethyl cellulose concentration) has 5 separate tumor ablations with the exception of 3% ethyl cellulose-ethanol injections at 0.1, 1.0 and 10 which were repeated 7 times.*$p<0.05$.

Normalized tumor volume at day 7 was used to quantify the dependence of therapeutic efficacy on injection rate and ethyl cellulose concentration (FIG. 7). Day 7 was chosen to observe the change in tumor volume to determine the effectiveness of the ablations (FIG. 6A and FIG. 6B). If the normalized tumor volume is 0%, the treatment has been completely effective. At day 7, the normalized tumor volume for 3% ethyl cellulose-ethanol was 25±43% and pure ethanol was 79±79% (p<0.01). The 10 mL/hr rate had the lowest overall mean at 13±23% as compared to manual injections at 89±78% (p<0.05). Of the 7 tumors injected with 3% ethyl cellulose-ethanol at 10 mL/hr, 6/7 completely regressed by day 7 and all 7 had completely regressed by day 8.

Figure 8A:
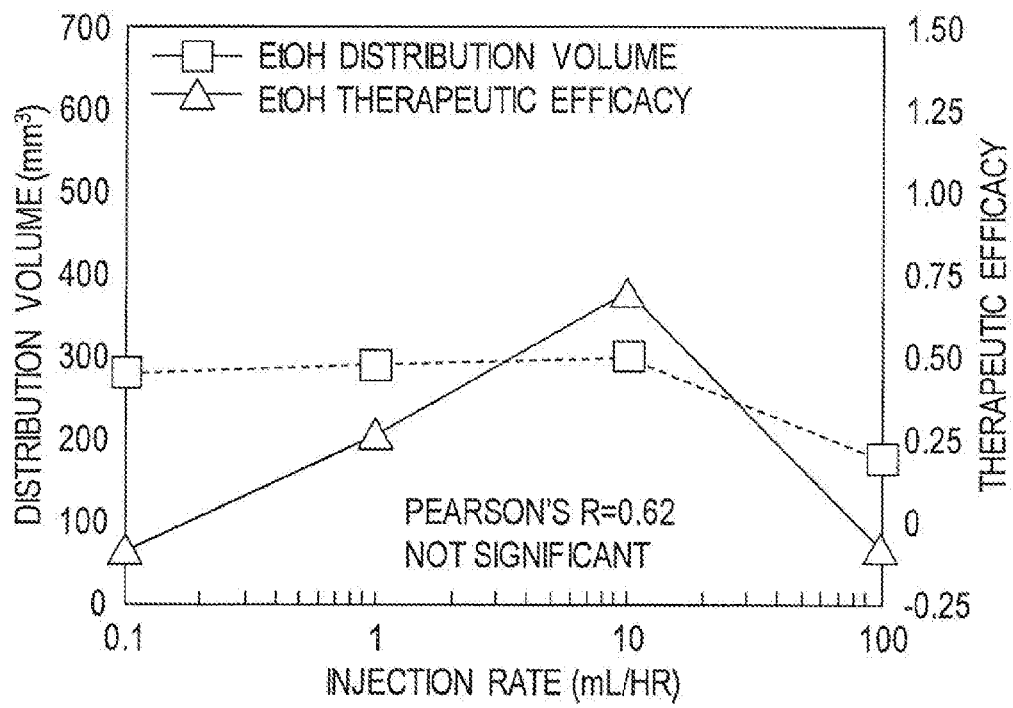
FIG. 8A FIG. 8B present graphs showing correlation between in vivo tumor ablations and mechanical phantom distribution volumes in accordance with an embodiment of the present disclosure. Therapeutic efficacy is defined as (1—normalized tumor volume at day 7). Mechanical phantom distribution volumes are only used from the rates that were used for the in vivo tumor ablations.
Figure 8B:
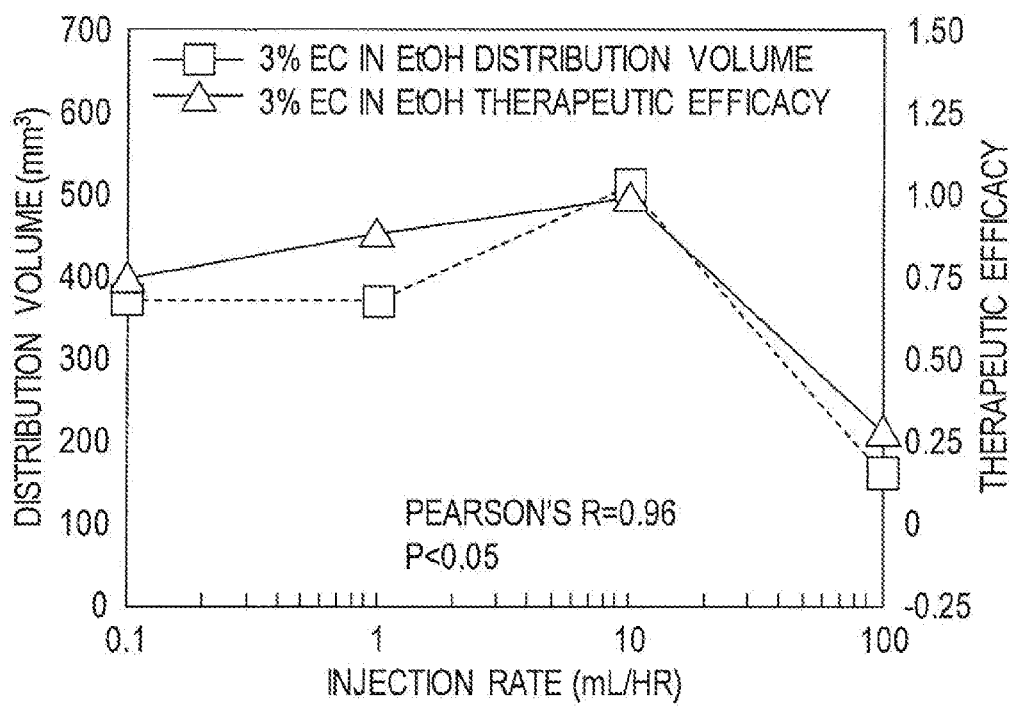

3.6. Correlation Between Mechanical Phantom and Therapeutic Efficacy Results Since both ethanol and 3% ethyl cellulose-ethanol solutions have comparable levels of cytotoxicity as shown in our viability study, therapeutic efficacy is ultimately determined by the distribution volume of the solution within the tumor. In the mechanical phantom, 3% ethyl cellulose-ethanol spread more than ethanol (421±350 mm$^3$ and 278±247 mm$^3$, p<0.01) and 3% ethyl cellulose-ethanol injections are more effective in vivo (25±43% vs. 79±79%, p<0.01). The phantom results also predict the dependence of therapeutic efficacy (quantified here as 1-normalized tumor volume at day 7) on injection rate. There is a strong correlation between efficacy and distribution volume for ethyl cellulose-ethanol (FIG. 8B, Pearson's coefficient=0.96, p<0.05). The correlation for ethanol alone is weaker (FIG. 8A, Pearson's coefficient 0.62, not significant), due to vascular clearance of slower injection rates (0.1 and 1.0 mL/hr) that was not predicted by the mechanical phantoms.

4. Discussion

Although the standard-of-care manual high-dosage pure ethanol ablation is effective in the treatment of capsulated liver tumors, it was ineffective in the treatment of epithelial tumors (FIG. 1) and resulted in complete regression of only 4 out of 13 tumors. The addition of ethyl cellulose, an ethanol-soluble and water-insoluble cellulose-derivative, increased efficacy (p<0.01, FIG. 7) likely because it increased viscosity but not because it increased cytotoxicity 3% ethyl cellulose-ethanol distributed over a large volume as measured in a tissue-mimicking mechanical phantom (p<0.01, FIG. 5B), because it decreased leakage through the injection site (FIG. 5A). In addition, ethyl cellulose-ethanol injections are better retained in the tumor due to the increased viscosity (FIG. 3A), which has been previously documented. Wang, Y., et al., *A novel method for viral gene delivery in solid tumors*. Cancer Res, 2005. 65(17): p. 7541-5. Furthermore, the hydrophobicity of ethyl cellulose causes a solution-to-gel phase transition in situ, which has been exploited in the treatment of venous malformations (without systemic side effects). Dompmartin, A., M. Vikkula, and L. M. Boon, *Venous malformation: update on aetiopathogenesis, diagnosis and management*. Phlebology, 2010. 25(5): p. 224-35. FIG. 3B shows the exponential increase in gel formation as a function of water concentration. As more water is added, the solution becomes more polar and the hydrophobic ethyl cellulose precipitates out of solution. At high water concentrations (>50%), the ethyl cellulose gel mass becomes much greater than the initial ethyl cellulose mass added to solution due to the absorption of ethanol. This gel will slowly release ethanol over time into the tumor and can be used in the future as an extended release system for hydrophobic drugs in vivo ethanol causes cell membrane disruption and likely increases extracellular water concentration enough to induce high rates of ethyl cellulose-ethanol gel formation. Turners are 80-90% water (Kiricuta, I. C., Jr. and V. Simplaceanu, *Tissue water content and nuclear magnetic resonance in normal and tumor tissues*. Cancer Res, 1975. 35(5): p. 1164-7), and the injected ethyl cellulose-ethanol volume is much lower than the total tumor volume, so it is likely that the resulting solution is high polar and large masses of gel form throughout the tumor. Ethyl cellulose is currently approved by the FDA as a food additive and costs less than $0.50/gram.

Therapeutic efficacy also depends on injection rate (FIG. 7) and reducing the injection rate from manual (approximately 100 mL/hr) to 10 mL/hr resulted in a significant improvement (p<0.01). This is most likely because higher injection rates cause higher pressures and increase likelihood of leakage out through the injection site (FIG. 5A) and crack formation in the tumor. Netti, P. A., et al., Role of extracellular matrix assembly in interstitial transport in solid tumors. Cancer Research, 2000. 60(9): p. 2497-2503. On the other hand, slower injections (0.1 mL/hr) were less effective than medium injection rates (10 mL/hr, p<0.1) because they 1) spread less than medium injection rates (FIG. 5, p<0.05) and 2) are more susceptible to vascular clearance. The non-linear relationship between intratumoral injection retention and rate has been demonstrated before (Wang, Y., et al., Effects of rate, volume, and dose of intratumoral infusion on virus dissemination in local gene delivery. Mol Cancer Ther, 2006. 5(2): p. 362-6), but the relationship between ablation efficacy and rate has not been investigated previously.

Overall, mechanical phantom results accurately predicted the dependence of efficacy on viscosity and injection rate. 3% ethyl cellulose-ethanol injections distributed over a larger volume in phantoms (p<0.01) and were more effective (p<0.01) than ethanol injections. Phantom results predicted the rate-dependence for 3% ethyl cellulose-ethanol (Pearson's coefficient=0.96, p<0.05), but not for ethanol (Pearson's coefficient 0.62, not significant) suggesting that a perfusion-free mechanical phantom recapitulates in vivo efficacy only for viscous solutions. Less viscous solutions may be impacted more by the presence of vasculature, especially at slower injection rates that are closer to the order of blood flow rates (FIG. 8A-FIG. 8B).

While we have demonstrated efficacy for epithelial tumor ablation and other applications have demonstrated the systemic safety of ethanol ablation in a variety of applications, more research is necessary to investigate the possibility of cervical stenosis and damage to underlying cervical muscle.

Our optimization has reduced the necessary volume to be injected and could circumvent some of the complications with leakage into surrounding tissue or circulation that traditional ethanol ablation faces. Traditional ethanol ablation injects up to 3 times the tumor volume in order to achieve efficacy, while we have demonstrated efficacy with approximately 25% of tumor volume. This allows for multiple injections for larger tumors while avoiding systemic complications.

Although our current focus is on epithelial lesions such as in the cervix and head and neck this treatment could be used in the treatment of larger lesions such as breast tumors, either in resource-limited settings where surgery is not an option or among patient populations that have non-aggressive tumors and are reluctant either to undergo surgery or make a return hospital visit after imaging.

5. Conclusion

We have demonstrated a significant improvement upon the standard-of-care manual ethanol ablation in a relevant preclinical model through the addition of ethyl cellulose and the reduction of injection rate. This improvement is not a result of increased cytotoxicity, but instead of enhanced fluid distribution and retention within the tumor. These findings are the foundation for a low-cost, accessible and effective cervical cancer treatment and could potentially be extended to other tumor types.

Example 2

Visualization of an Injected Fluorescein-Ethyl Cellulose-Ethanol Solution

Background: Addition of the fluorescent dye fluorescein to the therapy solution allows for visualization of the distribution of the delivered solution. Fluorescein is an FDA-approved fluorescent agent. Visualization of the distribution of the injected ablative solution can allow for real-time monitoring of the procedure.

Methods: Tumors implanted on the hind leg of mice were treated by intratumoral injection of a therapy solution combined with a fluorescent agent (fluorescein, 2.5% w/w) and imaged with a fluorescent imager. Visualization was performed in vivo from the surface of the tumor, as well as after the tumor had been excised, flash frozen and cut in half to obtain a cross-section.

Figure 10A:
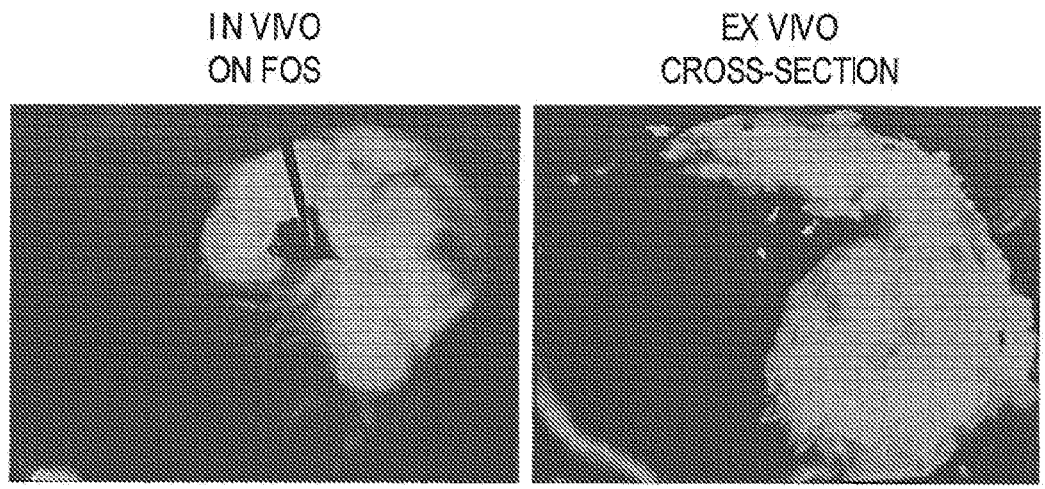
FIG. 10A-FIG. 10C present a comparison of visualization of an injected fluorescein-ethyl cellulose-ethanol solution with a fluorescent imager showing the correlation between on fos imaging from the exterior of the tumor in a live animal with imaging of the cross-section of the excised tumor in accordance with an embodiment of the present disclosure. This technique allows for visualization of the injected fluid distribution immediately after delivery.
Figure 10B:
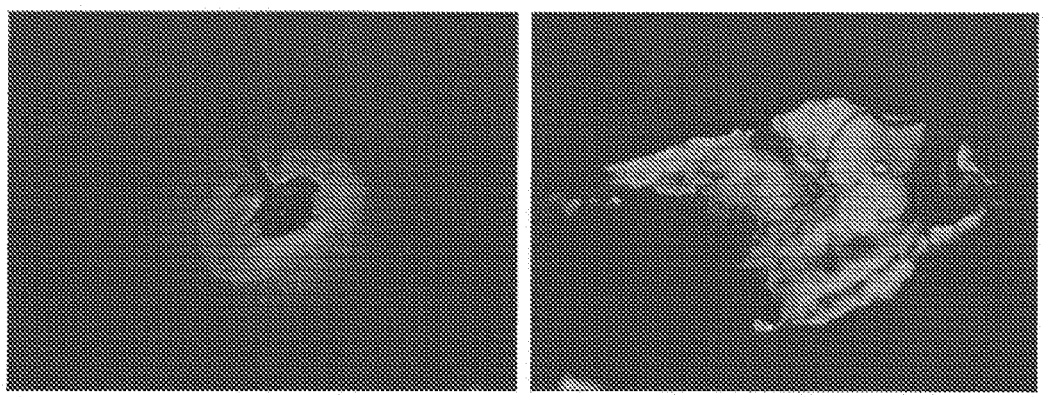
Figure 10C:
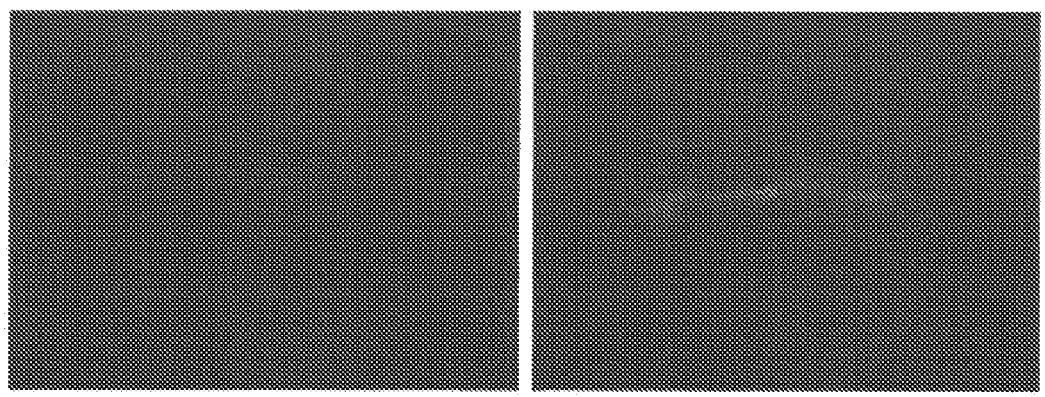

Findings: Qualitatively, and as seen in FIG. 10A-FIG. 10C, the signal obtained from the surface of the tumor correlated strongly with the signal obtained from the cross-sections.

Conclusion: The addition of a fluorescent agent such as fluorescein allows for in vivo, non-invasive visualization of the distribution of the injected ablative solution. This allows for real-time monitoring and modification of the procedure. This technique is low-cost and easy to perform.

Any patents or publications mentioned in this specification are indicative of the levels of those skilled in the art to which the invention pertains. These patents and publications are herein incorporated by reference to the same extent as if each individual publication was specifically and individually indicated to be incorporated by reference. In case of conflict, the present specification, including definitions, will control.

One skilled in the art will readily appreciate that the present invention is well adapted to carry out the objects and obtain the ends and advantages mentioned, as well as those inherent therein. The disclosure herein is presently representative of preferred embodiments, which are exemplary and not intended as limitations on the scope of the invention. Changes therein and other uses will occur to those skilled in the art which are encompassed within the spirit of the invention as defined by the scope of the claims.

We claim:

1. A method of treating a cancerous lesion or a precancerous lesion in a subject comprising administering to the subject a therapeutically effective amount of:
   a therapy solution, said therapy solution comprising a viscous carrier, wherein said viscous carrier comprises ethyl cellulose, and in which the concentration of ethyl cellulose in the therapy solution is at least 36% by weight; and
   an alcohol or hydrophobic agent, such that the lesion is treated,
   wherein the therapy solution is administered at a rate of from about 1 mL/hr to about 15 mL/hr.

2. The method of claim 1, wherein upon treating, lesion size is reduced.

3. The method of claim 1, wherein the lesion is a solid tumor.

4. The method of claim 1, wherein the lesion is a non-capsulated tumor.

5. The method of claim 1, wherein the lesion is a precancerous lesion.

6. The method of claim 1, wherein the therapy solution comprises the hydrophobic agent, and the hydrophobic agent is a hydrophobic anti-cancer drug.

7. The method of claim 1, wherein the therapy solution comprises the alcohol.

8. The method of claim 1, wherein the lesion is a carcinoma, lymphoma, blastoma, or sarcoma.

9. The method of claim 1, wherein the lesion is a breast cancer, prostate cancer, colon cancer, squamous cell cancer, small-cell lung cancer, non-small cell lung cancer, ovarian cancer, cervical cancer, gastrointestinal cancer, pancreatic cancer, liver cancer, bladder cancer, hepatoma, colorectal cancer, uterine cervical cancer, endometrial carcinoma, salivary gland carcinoma, kidney cancer, vulval cancer, pancreatic cancer, thyroid cancer, hepatic carcinoma, skin cancer, melanoma, myeloma, head and neck cancer, or Ewing sarcoma.

10. The method of claim 1, wherein the lesion is an epithelial tumor or precancerous epithelial lesion along a lumen of the body.

11. The method of claim 1, wherein the lesion is a cervical cancer, a head and neck cancer, an oral cancer or a precancerous lesion thereof.

12. The method of claim 1, wherein the lesion is a cervical cancer or a cervical precancerous lesion.

13. The method as in claim 1 in which the therapy solution is administered by injection.

14. The method according to claim 1 in which the therapy solution is injected or infused directly into the lesion at one or more sites.

15. The method according to claim 1 in which about 1 mL to about 10 mL of the therapy solution is administered.

16. The method according to claim 1, wherein the therapy solution further comprises a detectable compound.

17. The method according to claim 16, wherein the detectable compound comprises a fluorescent compound.

18. The method according to claim 16, wherein said method further comprises imaging the lesion to monitor distribution of the therapy solution in vivo upon administration, and/or during administration in real time.

19. The method according to claim 1 in which the concentration of ethyl cellulose in the therapy solution is at least 6% to about 10% by weight.

20. The method according to claim 1 in which the concentration of ethyl cellulose in the therapy solution is about 8% by weight.

21. The method according to claim 1 in which the concentration of ethyl cellulose in the therapy solution is about 10% by weight.

* * * * *

UNITED STATES PATENT AND TRADEMARK OFFICE
CERTIFICATE OF CORRECTION

PATENT NO. : 12,350,341 B2
APPLICATION NO. : 16/490227
DATED : July 8, 2025
INVENTOR(S) : Morhard et al.

It is certified that error appears in the above-identified patent and that said Letters Patent is hereby corrected as shown below:

In the Specification

Column 1, Line 32: Please correct "leading," to read --leading--

Column 2, Lines 39-40: Please correct "ethyl methyl cellulose, in" to read --ethyl methyl cellulose. In--

Column 4, Line 2: Please correct "50 trim³" to read --50 mm3--

Column 5, Line 13: Please correct "100" to read --100 mL/hr--

Column 5, Line 19: Please correct "10" to read --10 mL/hr,--

Column 5, Line 29: Please correct "Pt arson's" to read --Pearson's--

Column 5, Line 61: Please correct "van" to read --can--

Column 6, Line 51: Please correct "cancer/lesion," to read --cancer/lesion--

Column 8, Line 56: Please correct "[Arai on" to read --[Artifon,--

Column 8, Line 58: Please correct "Enclose," to read --Endosc,--

Column 9, Line 14: Please correct "201.96(9):" to read --2011. 96(9):--

Column 9, Line 54: Please correct ""Ugh Human Development"" to read --"High Human Development."--

Column 10, Line 20: Please correct "Int Gynaecol Obstet," to read --Int J Gynaecol Obstet,--

Signed and Sealed this
Seventh Day of October, 2025

John A. Squires
*Director of the United States Patent and Trademark Office*

CERTIFICATE OF CORRECTION (continued)
U.S. Pat. No. 12,350,341 B2

Column 10, Line 52: Please correct "2011.20(3):" to read --2013. 20(3):--

Column 11, Line 2: Please correct "6.1(4):" to read --61(4):--

Column 11, Line 16: Please correct "Gibeo," to read --Gibco,--

Column 11, Line 35: Please correct "0-5%" to read --0.5%--

Column 11, Line 35: Please correct "(Gibed," to read --(Gibco,--

Column 13, Line 13: Please correct "1, 2 4 and 7 days" to read --1, 2, 4 and 7 days--

Column 15, Lines 18-19: Please correct "Pearson's coefficient 0.62," to read --Pearson's coefficient=0.62,--

Column 15, Line 56: Please correct "drugs in vivo" to read --drugs. In vivo,--

Column 16, Lines 27-28: Please correct "(Pearson's coefficient 0.62," to read --(Pearson's coefficient=0.62,--

In the Claims

Column 17, Line 51, Claim 1: Please correct "36%" to read --6%--